(12) United States Patent
George et al.

(10) Patent No.: US 11,168,360 B2
(45) Date of Patent: Nov. 9, 2021

(54) CIRCULARIZATION METHODS FOR SINGLE MOLECULE SEQUENCING SAMPLE PREPARATION

(71) Applicant: Roche Sequencing Solutions, Inc., Pleasanton, CA (US)

(72) Inventors: Michael George, Davis, CA (US); Jenny A. Johnson, Castro Valley, CA (US); Duylinh Nguyen, American Canyon, CA (US); Ulrich Schlecht, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 30 days.

(21) Appl. No.: 16/813,481

(22) Filed: Mar. 9, 2020

(65) Prior Publication Data

US 2020/0208208 A1    Jul. 2, 2020

Related U.S. Application Data

(63) Continuation of application No. PCT/EP2018/076977, filed on Oct. 4, 2018.

(60) Provisional application No. 62/569,475, filed on Oct. 6, 2017.

(51) Int. Cl.
| | | |
|---|---|---|
| *C12Q 1/6806* | (2018.01) | |
| *C12Q 1/6851* | (2018.01) | |
| *C12Q 1/6855* | (2018.01) | |
| *C12N 15/66* | (2006.01) | |
| *C12P 19/34* | (2006.01) | |

(52) U.S. Cl.
CPC ......... *C12Q 1/6855* (2013.01); *C12N 15/66* (2013.01); *C12P 19/34* (2013.01); *C12Q 1/6806* (2013.01); *C12Q 1/6851* (2013.01)

(58) Field of Classification Search
CPC .. C12Q 1/6806; C12Q 1/6851; C12Q 1/6855; C12Q 2521/319; C12Q 2521/501; C12Q 2525/155; C12Q 2525/161; C12Q 2525/191; C12Q 2525/307; C12Q 2533/101; C12Q 2535/122; C12P 19/34; C12N 15/66

See application file for complete search history.

(56) References Cited

U.S. PATENT DOCUMENTS

| | | | | |
|---|---|---|---|---|
| 8,968,999 | B2 * | 3/2015 | Gibson | .................. C12N 15/10 435/6.1 |
| 9,657,291 | B2 * | 5/2017 | Li | ........................ C12Q 1/6874 |
| 2004/0110153 | A1 | 6/2004 | Dong | |
| 2012/0231508 | A1 | 9/2012 | Chiu | |
| 2014/0329282 | A1 * | 11/2014 | Nelson | ................. C12Q 1/6855 435/91.2 |

FOREIGN PATENT DOCUMENTS

| | | |
|---|---|---|
| WO | 2013036685 A1 | 3/2013 |
| WO | 2015148219 A1 | 10/2015 |

OTHER PUBLICATIONS

International Search Report and Written Opinion, dated Nov. 6, 2018, in corresponding PCT/EP2018/076977, filed Oct. 4, 2018, pp. 1-16.

\* cited by examiner

*Primary Examiner* — David C Thomas

(74) *Attorney, Agent, or Firm* — Eric Grant Lee; Olga Kay

(57) ABSTRACT

The invention is a novel method of making and using a library such as a sequencing library of single stranded circular nucleic acid templates via splint ligation.

11 Claims, 9 Drawing Sheets

1. Nick and exo-chew one of the two strands
2. Nick and extension from nicked position

CIRCULARIZATION METHODS FOR SINGLE MOLECULE SEQUENCING SAMPLE PREPARATION

CROSS-REFERENCE TO RELATED APPLICATIONS

This application is a continuation of the International Application Ser. No. PCT/EP/2018/076977 filed on Oct. 4, 2018, which claims priority to the U.S. Provisional Application Ser. No. 62/569,475 filed on Oct. 6, 2017 both of which are incorporated herein by reference.

FIELD OF THE INVENTION

The invention relates to the field of nucleic acid analysis and more specifically, to preparing circular templates for nucleic acid sequencing.

BACKGROUND OF THE INVENTION

Circular nucleic acid templates have multiple uses in nucleic acid analysis. Linear nucleic acids are converted into a circular form for amplification, e.g., by rolling circle amplification (RCA) and subsequent detection and quantification, see U.S. Pat. No. RE44265. The use of circular templates in sequencing is also known in the art. See U.S. Pat. Nos. 7,302,146 and 8,153,375. These strategies create a circular template comprising both strands of the target nucleic acid. The present invention is a novel efficient method of creating a library of templates suitable for sequencing comprising circular single stranded molecules form each strand of the target nucleic acid. The method allows the creation of templates of virtually unlimited length.

SUMMARY OF THE INVENTION

The invention is a method of forming a circular nucleic acid molecule or a library of circular molecules for nucleic acid sequencing.

In some embodiments, the invention is a method of forming a circular molecule from a target nucleic acid, comprising: attaching adaptor sequences to the ends of the target nucleic acid to form an adapted target nucleic acid; contacting the adapted target nucleic acid with a double stranded backbone nucleic acid; generating single stranded overhangs in both the backbone and the adapted target nucleic acid; hybridizing the single stranded overhangs of the backbone with the single stranded overhangs of the adapted target nucleic acid; ligating the ends of the backbone with the ends of the adapted target nucleic acid to form a circular molecule. In some embodiments the adaptors are attached to the ends of the target nucleic acid by ligation. In other embodiments, the adaptors are attached to the ends of the target nucleic acid by extension of a target specific bipartite primer comprising adaptor sequences in the 5'-portion. The adapted target nucleic acid is amplified prior to being contacted with the backbone.

In some embodiments, the adaptor and the backbone comprise complementary terminal sequences. The single stranded overhangs are generated by nuclease digestion. The backbone and adaptor sequences comprise exonuclease nuclease-resistant modifications such as nucleotides with phosphorothioate linkage. In some embodiments, the method further comprises a polymerase fill in step prior to ligation.

In some embodiments, the invention is a method of sequencing a target nucleic acid comprising forming a circular molecule from a target nucleic acid as described herein. The method can include the steps of: attaching adaptor sequences to the ends of the target nucleic acid to form an adapted target nucleic acid; contacting the adapted target nucleic acid with a double stranded backbone nucleic acid; generating single stranded overhangs in both the backbone and the adapted target nucleic acid; hybridizing the single stranded overhangs of the backbone with the single stranded overhangs of the adapted target nucleic acid; ligating the ends of the backbone with the ends of the adapted target nucleic acid to form a circular molecule; separating the strands of the circular molecule to generate single stranded circular molecules; and annealing a sequencing primer to each of the single stranded circular molecule; extending the annealed sequencing primer thereby sequencing the target nucleic acid. The adaptor may comprise a sequencing primer binding site and at least one barcode. In some embodiments, the backbone comprises at least one barcode. The strands of the nucleic acid can be separated by heat, or chemical means, or by nicking one strand and removing the nicked strand by exonuclease digestion, e.g., if the backbone comprises at least one deoxyuracil and the sample is contacted by Uracil-N-DNA glycosylase. In some embodiments, the backbone comprises a ligand for a capture moiety and one strand of the ligated circular molecule is captured on solid support.

In some embodiments, the sequencing utilizes a strand displacing DNA polymerase. In some embodiments, the sequencing utilizes a nanopore device.

In some embodiments, the method further comprises a purification step after the ligation step.

DETAILED DESCRIPTION OF THE INVENTION

Definitions

Figure 1:
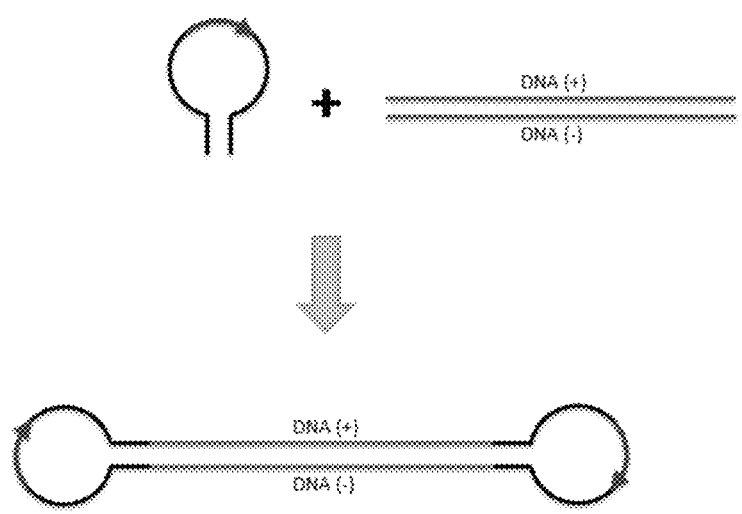
FIG. 1 shows the prior art strategy of creating circular templates for sequencing.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, through in vitro addition to) different target nucleic acids. The universal priming site is added to the plurality of target nucleic acids using adaptors or using target-specific (non-universal) primers having the universal priming site in the 5'-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

The terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may also have only one cycle (making a single copy of the target nucleic acid). The copy may have additional sequences, e.g., those present in the primers used for amplification.

The term "sequencing" refers to any method of determining the sequence of nucleotides in the target nucleic acid.

The term "Gibson assembly" is a method of isothermal in vitro recombination described e.g., in Gibson et al., (2009), *Enzymatic assembly of DNA molecules up to several hundred kilobases*, Nature Methods, 6(5): 343-348 and U.S. Pat. No. 8,968,999. The method generally comprises joining (assembling) nucleic acids via the steps of exonuclease digestion to create at least partially cohesive ends, annealing of ends, polymerase fill and ligation of ends.

The term "stitch adaptor" refers to adaptor having sequences complementary to those in the ends of the backbone oligonucleotide. When rendered single-stranded, e.g., by an exonuclease, the terminal portions (ends) of the adapted nucleic acids are capable of hybridizing with the ends of the backbone. The stitch adaptor may contain additional useful elements such as barcodes and primer binding sites. The stitch adaptor may also contain modified nucleotides.

The term "backbone" refers to an oligonucleotide or a nucleic acid facilitating the self-ligation of another nucleic acid into a circle. Generally the backbone is designed to have sequences complementary to those in the ends of the other nucleic acid, e.g., adaptor sequences. When rendered single-stranded, e.g., by an exonuclease, the terminal portions (e.g., 3'-terminal portions) of the backbone are capable of hybridizing with the 3'-terminal portions of the adapted nucleic acids. The backbone may contain additional useful elements such as barcodes and primer binding sites. The backbone may also contain modified nudeotides. The backbone could be of different length (e.g. 200, 500, 1000, 2000 bp), based on which is most suitable for circularization of a particular set of target nucleic acids.

As used herein, the term "complementary" in reference to double stranded nucleic acids refers to double stranded nucleic acids capable of generating complementary single strands. For example, when one or more nucleotides are removed from the 5'-ends, the exposed 3'-end overhangs are capable of hybridizing to each other.

The present invention is a method of making circular target nucleic acid molecules and libraries of such molecules for downstream analysis such as nucleic acid sequencing. Briefly, the method utilizes amplified target nucleic acid that has adaptor sequences introduced by either adaptor ligation or amplification with tagged gene-specific primers. The double stranded amplified target nucleic acid is contacted with a backbone oligonucleotide. The target and the backbone are rendered partially single stranded. The partially single-stranded target nucleic acids are annealed and ligated to create a circular nucleic acid comprising the target sequence. Each strand of the double stranded circle comprises a primer binding site for independent downstream analysis such as sequencing.

The method of the invention may be used as a sample preparation method for single molecule sequencing (SMS) platforms. The double-stranded circular DNA molecules contain sequencing primer binding sites on both strands and therefore facilitate circular sequencing of both, plus- and minus-strand, independently of each other.

The method has advantages over existing circularization methods, See U.S. Pat. Nos. 7,302,146 and 8,153,375. The current method to generate single stranded circular DNA templates for SMS involves ligation of a double-stranded target to two hairpin adaptors, each which contains the sequencing primer binding site. In this approach the circular consensus sequence is derived from sequencing the plus-and minus-strand joined together (FIG. 1).

The method utilizes a backbone oligonucleotide to facilitate ligation which is similar to the "vector" oligonucleotide used e.g., in US2012003657 (see FIG. 1A therein). The method of the present invention is a major improvement in efficiency over the prior art bimolecular ligation because it utilizes Gibson assembly including partial exonuclease digestion to facilitate the assembly or circles.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples). The sample may comprise whole blood or blood fractions where tumor cells may be present. In some embodiments, the sample, especially a liquid sample may comprise cell-free material such as cell-free DNA or RNA including cell-free tumor DNA or tumor RNA. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, induding a single nucleotide polymorphism or variant (SNP of SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded DNA such as the one founds in preserved samples. In other embodiments, the target nucleic acid is fragmented in vitro, e.g., by physical means such as sonication or by endonuclease digestion, e.g., restriction digestion.

In some embodiments, the invention is a method comprising a step of amplifying the target nucleic acid. The amplification may be by polymerase chain reaction (PCR) or any other method that utilizes oligonucleotide primers. Various PCR conditions are described in *PCR Strategies* (M. A. Innis, D. H. Gelfand, and J. J. Sninsky eds., 1995, Academic Press, San Diego, Calif.) at Chapter 14*PCR Protocols:A Guide to Methods and Applications* (M. A. Innis, D. H. Gelfand, J. J. Sninsky, and T. J. White eds., Academic Press, NY, 1990).

The amplification may utilize bipartite amplification primers comprising a target-specific sequence and a sequence of the stitch adaptor to generate double stranded amplicons. In some embodiments, a defined target or group of target nucleic acids is being interrogated. In such embodiments, target specific amplification primers may be used. A primer may have a bipartite structure composed of a target-specific sequence in the 3'-portion and an adaptor sequence in the 5'-portion. Typically, the target-specific primers are used as a pair of distinct oligonucleotides, e.g., a forward and a reverse primer. For subsequent steps, a different universal sequence can be added to the forward and the reverse primer in order to distinguish the complementary strands (i.e., the (+) and the (−) strands) in subsequent steps of the method. In some embodiments, the universal sequence of the bipartite primers comprises a sequencing primer binding site.

Adaptors are introduced into the target nucleic acids either by primer extension or by ligation. In some embodiments, the primer extension is a single round. In other embodiment, the primer extension goes through multiple cycles, e.g., PCR amplification.

The resulting target nucleic acid comprises a target sequence flanked by the adaptor sequences. The adaptors comprise the portion used for circularization (matching the backbone sequences). In some embodiments, adaptors contain primer binding sites for downstream steps, e.g., amplification primer binding sites and sequencing primer binding sites.

Figure 2:
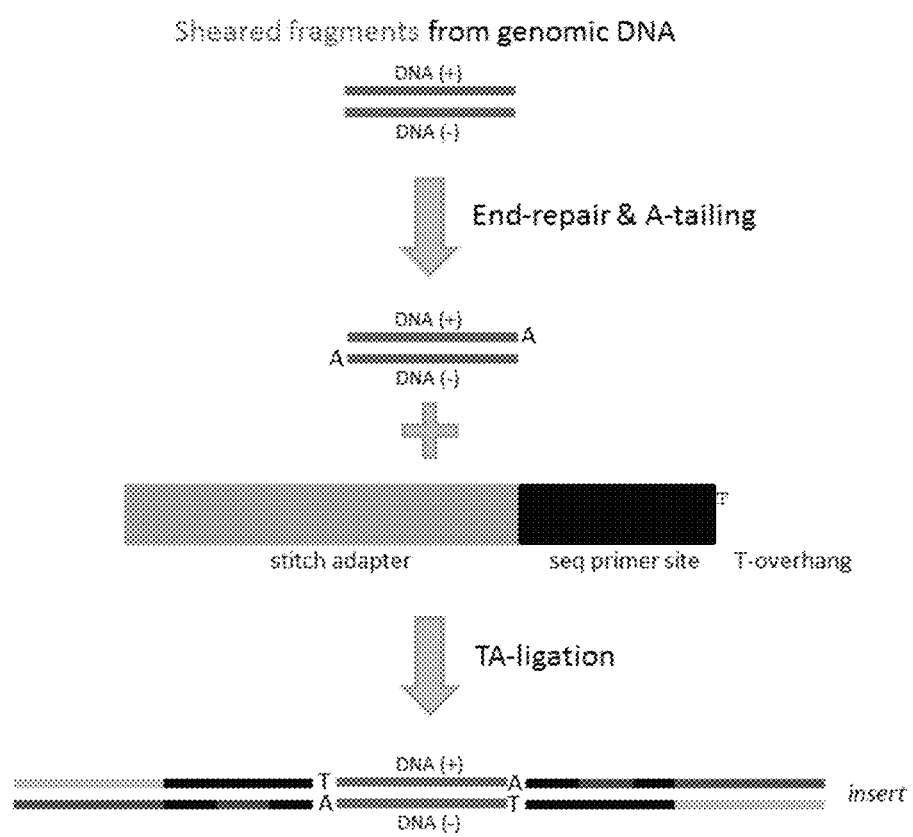
FIG. 2 shows step 1 of the method: ligating universal adaptors with sequencing primers sites.
Figure 7:
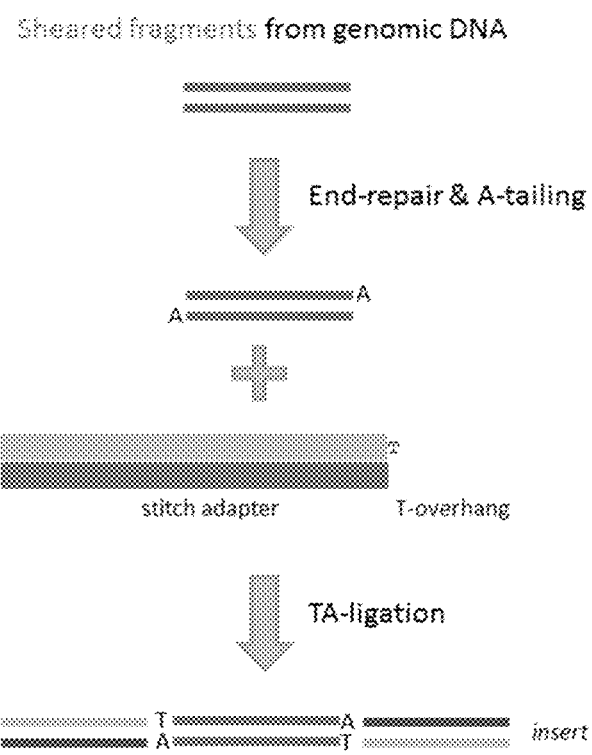
FIG. 7 shows alternative step 1 of the method: ligating universal adaptors with no sequencing primers sites.

In some embodiments, the target nucleic acid is ligated to adaptors. (FIGS. 2, 7). The ligation can be a blunt-end ligation or a more efficient cohesive-end ligation. The target nucleic acid or the adaptors may be rendered blunt-ended by strand-filling, i.e., extending a 3'-terminus by a DNA polymerase to eliminate a 5'-overhang or digesting the 3'-overhang with a 3'-5'-ecxonuclease activity. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In each of the above embodiments, the adaptor molecule may acquire the desired ends (blunt, single-base extension or multi-base overhang) by design of the synthetic adaptor oligonucleotides further described below.

In some embodiments, the overhang sequences in the adaptor contain a modified nucleotide that modifies the stability of the hybridization complex between the ends of the adaptor and the target molecule. The modified bases may include one or more of the following: G-clamps, inosine, methyl-dC, propynyl-pyrimidine (propynyl-dU or dC).

In some embodiments, the overhang sequences in the adaptor contain exonuclease inhibitors, e.g., phosphorothioate nucleotides.

In some embodiments, other enzymatic steps may be required to accomplish the ligation. In some embodiments, a polynucleotide kinase may be used to add 5'-phosphates to the target nucleic acid molecules and adaptor molecules.

In some embodiments, the adaptor molecules are in vitro synthesized artificial sequences. In other embodiments, the adaptor molecules are in vitro synthesized naturally-occurring sequences known to possess the desired secondary structure. In yet other embodiments, the adaptor molecules are isolated naturally occurring molecules or isolated non naturally-occurring molecules.

Figure 3:
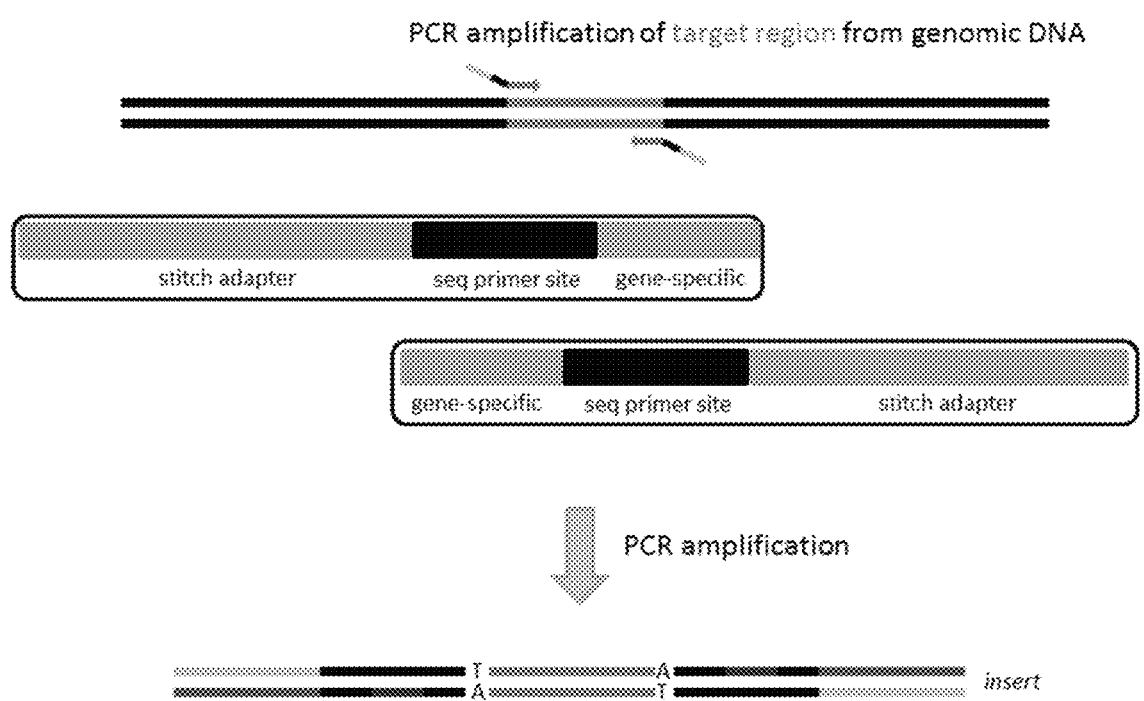
FIG. 3 shows alternative step 1 of the method: amplification with tagged gene specific primers having sequencing primer sites.
Figure 8:
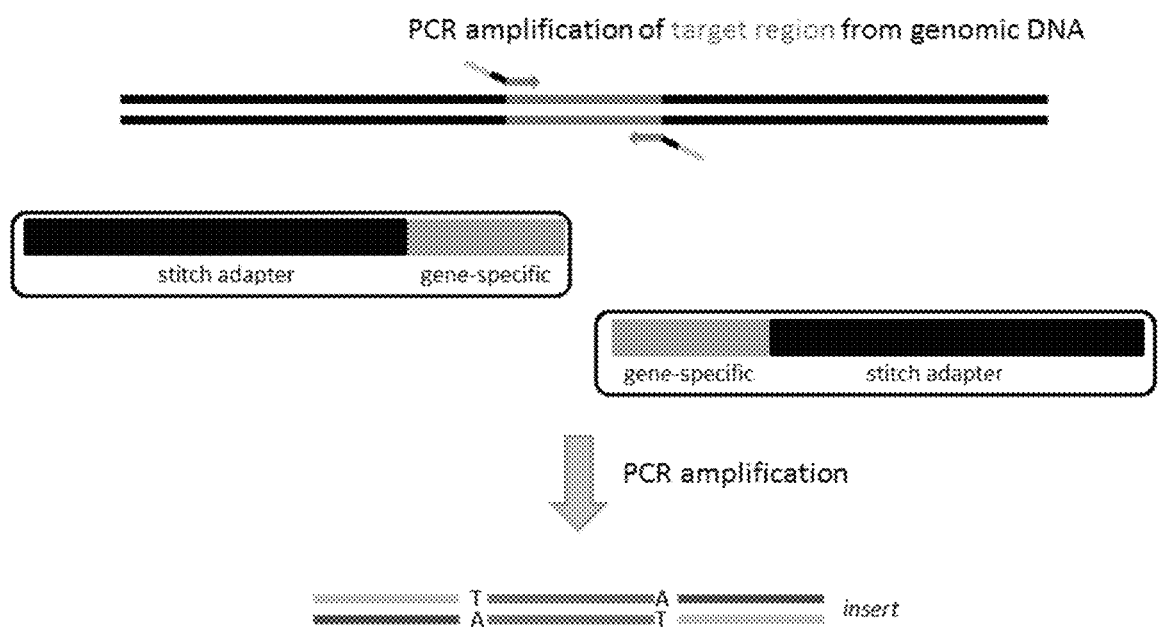
FIG. 8 shows alternative step 1 of the method: amplification with tagged gene specific primers with no sequencing primers sites.

In some embodiments, adaptor sequences e.g., stitch adaptor sequences and sequencing primer binding sites are added to the target nucleic acid through the use of bipartite primers containing such sequences sin the 5'-portion of the primer. (FIGS. 3, 8).

In some embodiments, the invention comprises introduction of barcodes into the target nucleic acids. Sequencing individual molecules typically requires molecular barcodes such as described e.g., in U.S. Pat. Nos. 7,393,665, 8,168, 385, 8,481,292, 8,685,678, and 8,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, bi-partite amplification primers comprise one or more barcodes. In other embodiments, adaptors comprise one or more barcodes. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID.

In some embodiments, each barcode comprises a pre-defined sequence. In other embodiments, the barcode comprises a random sequence. Barcodes can be 1-20 nucleotides long.

Figure 4:
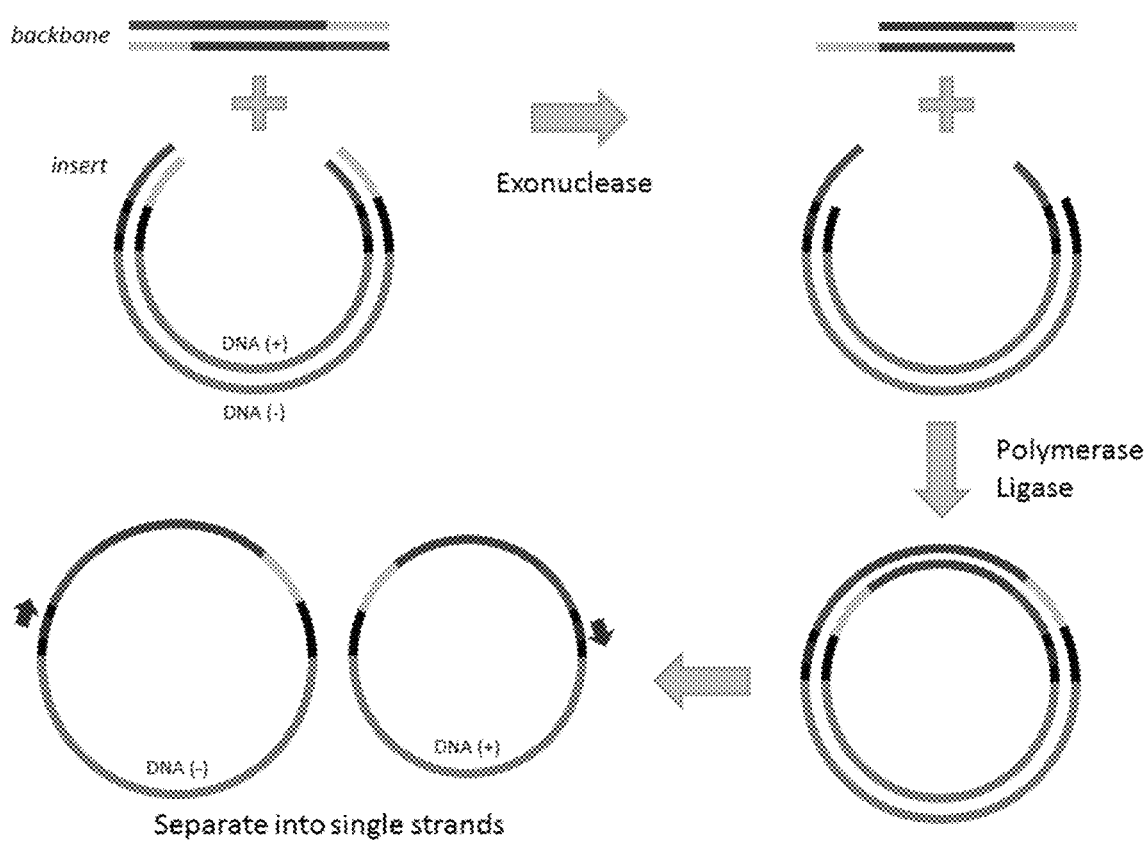
FIG. 4 shows step 2 of the method: exonuclease digestion and circularization.
Figure 5:
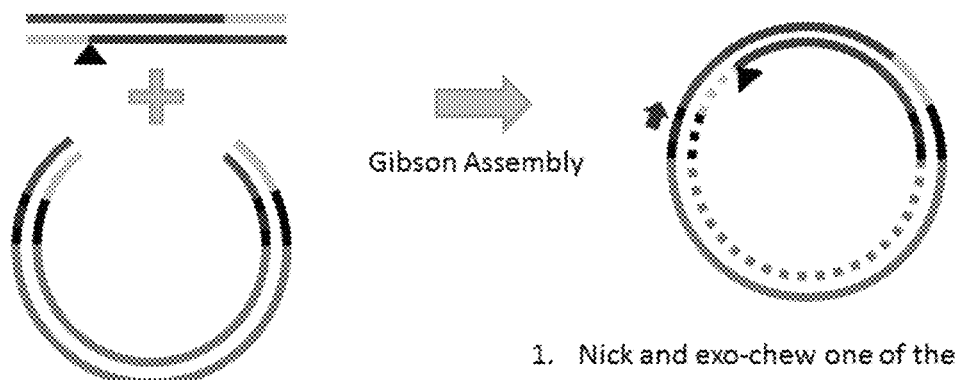
FIG. 5 shows alternative step 2 of the method: circularization using Gibson assembly.
Figure 6:
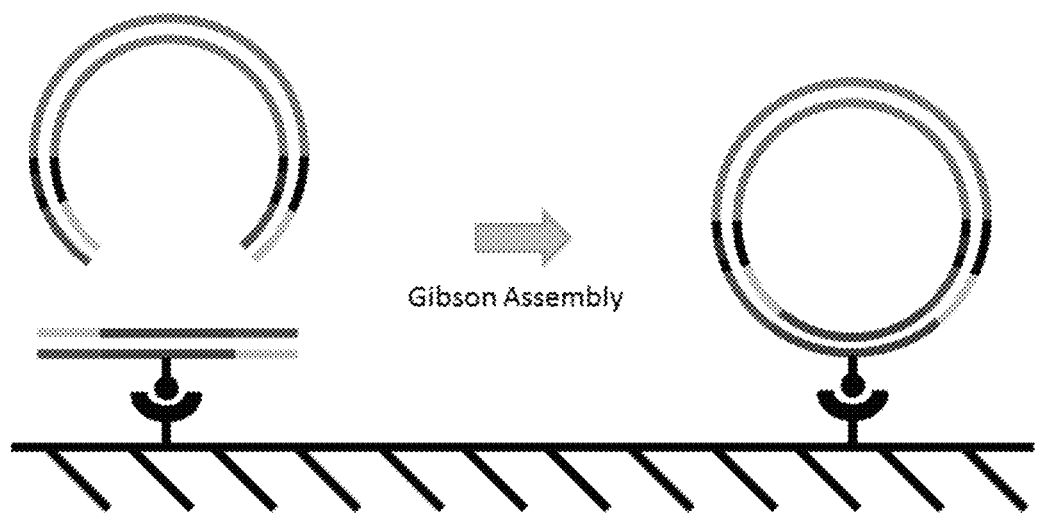
FIG. 6 shows alternative step 2 of the method: circularization using Gibson assembly with capture on solid support.
Figure 9:
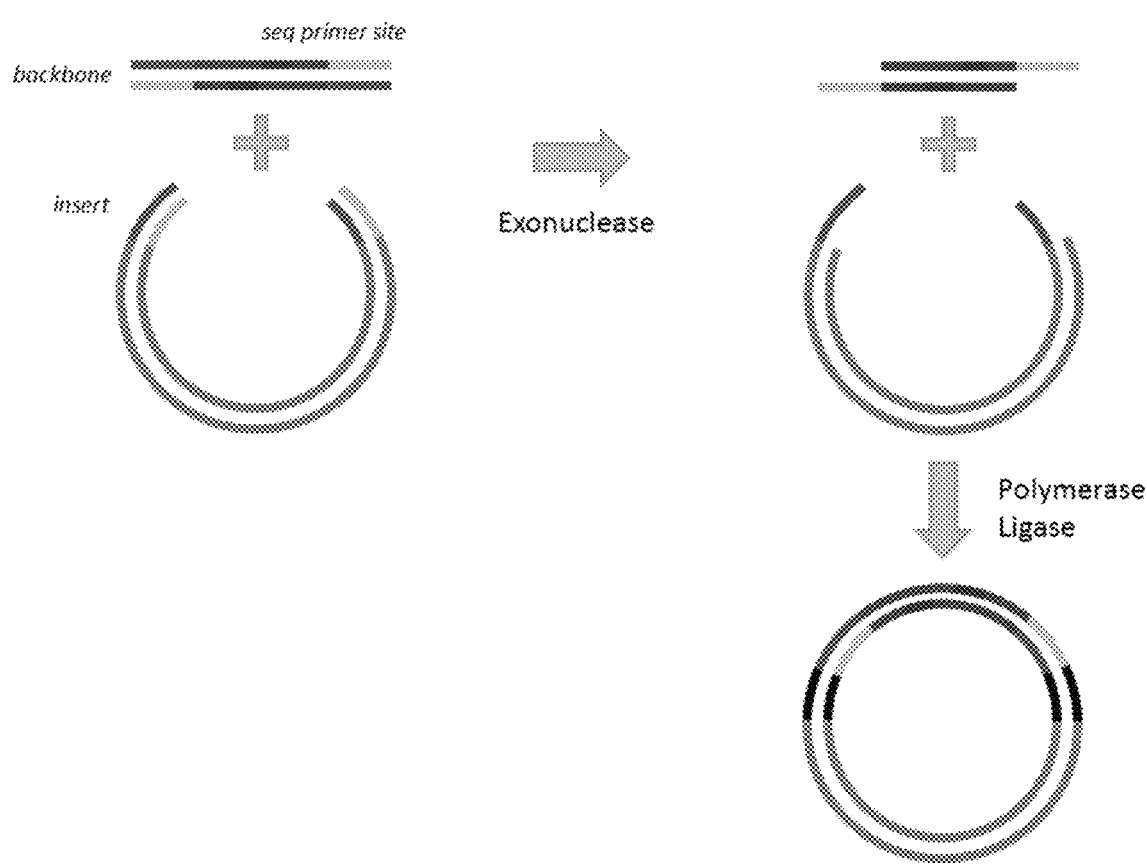
FIG. 9 shows alternative step 2 of the method: circularization using Gibson assembly where the backbone comprises a sequencing primer site.

In some embodiments, the invention utilizes a backbone oligonucleotide, an oligonucleotide or a nucleic acid facilitating the self-ligation of another nucleic acid into a circle. (FIGS. 4, 5, 6). Generally the backbone is designed to have sequences complementary to those in the ends of the other nucleic acid, e.g., adaptor sequences. When rendered single-stranded, e.g., by an exonuclease, the terminal sequences of the backbone are capable of annealing to the single stranded terminal sequences of the adapted nucleic acids. In some embodiments, the single stranded 3'-terminal sequences of one molecule are complementary to the single stranded 3'-sequences of the other molecule so that the two single stranded portions could anneal and form a double stranded structure. The backbone may contain useful elements such as barcodes and primer binding sites. (FIGS. 4, 5, 6). In some embodiments, the backbone contains only the stitch adaptor sequences used for circularization (FIG. 7). In some embodiments, the backbone comprises the sequencing primer binding site (FIG. 9).

In some embodiments, the backbone contains modified nucleotides. The backbone could be of different length (e.g. 200, 500, 1000, 2000 bp), based on which is most suitable for circularization of a particular set of target nucleic acids.

In some embodiments, the backbone comprises a ligand for a capture moiety as described herein below. FIG. 6.

In some embodiments, the method interrogates only one of the two strands of the target nucleic acid or analyzes the two strands separately. The invention comprises a step of separating the strands of the double stranded amplicons. The two strands may be separated by physical means, i.e., alkaline denaturation or heat denaturation.

In other embodiments, the strands are separated enzymatically when one strand is degraded e.g., by a combination of endonuclease and exonuclease. In some embodiments, a nick I introduced into one strand e.g., through the use of deoxyuracils incorporated into one strand of the backbone. The uracil is then excised by Uracil-N-DNA glycosylse (UNG) and the strand with the phosphodiester bond at the resulting abasic site is broken e.g., by heat treatment resulting in the nick. An exonuclease is then added to degrade the nicked strand leaving the complementary stand intact for further analysis. (FIG. 5).

In yet other embodiments, a desired strand is captured with an affinity reagent capable of selectively binding a strand with the affinity ligand.

In some embodiments, the ends of the nucleic acid are phosphorylated. In some embodiments, the 5'-end of one primer is phosphorylated in order to enable the subsequent ligation step. Phosphorylation of the primer, or the adaptor can be performed e.g., with the use of a polynucleotide kinase (PNK) such as T4 PNK.

In some embodiments, the ends of the nudeic acid comprise a modified nucleotide that protects the strand from nuclease digestion. In some embodiments, the strand comprises one or more phorphorothioate nucleotides.

The invention utilizes a method of joining nudeic acid molecules known as Gibson Assembly, which is an isothermal in vitro recombination methods described in Gibson et al., (2009) *Enzymatic assembly of DNA molecules up to several hundred kilobases*, Nature Methods, 6(5): 343-348 and U.S. Pat. No. 8,968,999.

In some embodiments, the method comprises assembling DNA fragments having complementary terminal sequences such as the backbone oligonucleotide and the adapted target nucleic acids as described herein. In the first step, an exonuclease removes one or more nucleotides from the ends of the nucleic acids. In some examples, the nucleotides are removed from the 5'-end. In some embodiments, the exonuclease possesses a 5'-3'-exonuclease activity. In some embodiments, the exonuclease is a viral exonuclease or a recombinantly produced viral exonuclease such as T5 exonuclease. The exonuclease treatment creates single-stranded DNA overhangs which are complementary between the backbone and the adapted target nucleic acid. Next, the complementary ends are annealed. In some embodiments, the annealed structure comprises gaps that are filled by a DNA polymerase. In some embodiments, the polymerase is a high fidelity DNA polymerase possessing 3'-5'-exonuclease activity. In some embodiments, the polymerase is (or has the activity of) an archaeal polymerase such as Pfu polymerase or its derivative.

The invention further comprises a ligation step comprising ligating the 5'-and 3'-ends of the annealed (an optionally extended) strands thereby forming a circular molecule comprising adaptor sequences, target nucleic acid sequences and backbone sequences. In some embodiments, the ligase is an *E. coli* or an archaeal ligase such as *Taq* DNA ligase.

In some embodiments, the invention comprises an exonuclease digestion step wherein the linear nucleic acids possibly comprising excess backbone oligonucleotides or un-circularized adapted target nucleic acids are removed from the reaction mixture. In some embodiments, the exonucleases are Exo III, Exo VII or a mixture thereof.

In some embodiments, the backbone oligonudeotide is linked to a solid support via a capture moiety. In some embodiments, the ligand-capture moiety pair is selected from biotin-streptavidin, antibody-antigen or conjugated oligonudeotide-complementary capture oligonudeotide. In such embodiments, the purification step comprises a step of removal of any nucleic acid not bound to solid support.

In some embodiments, the invention is a method of making a library of circular nucleic acids from a mixture of diverse target nucleic acids in a sample. The method comprises a step of attaching adaptors to the target nucleic acid molecules in the sample by a sequence-independent manner such as ligation. In some embodiments, adaptors comprise universal primer binding sites so that ligation products could be amplified prior to subsequent steps.

In some embodiments, adaptors comprise primer binding sites and amplification primers comprise stitch adaptor sequences in the 5'-portion of the primer. The resulting adapted target molecules or amplicons thereof comprise target sequences flanked by stitch adaptor sequences. The backbone oligonudeotide comprises terminal sequences that are complementary to the sequences contained in the adaptors. The adapted target molecules or amplicons thereof are then subjected to the steps of the circularization steps with a backbone oligonucleotide described herein to generate a library of circular target nucleic acid molecules.

In some embodiments, the present invention comprises detecting target nucleic acids in a sample by nucleic acid sequencing. Multiple nucleic acids, including all the nucleic acids in a sample may be converted into the template configuration of the invention and sequenced. In some embodiments, the template is a library of circular molecules formed as described herein and subjected to nucleic acid sequencing.

Sequencing can be performed by any method known in the art. Especially advantageous is the high-throughput single molecule sequencing. Examples of such technologies include the Illumina HiSeq platform (Illumina, San Diego, Calif.), Ion Torrent platform (Life Technologies, Grand Island, N.Y.), Pacific BioSciences platform utilizing the SMRT (Pacific Biosciences, Menlo Park, Calif.) or a platform utilizing nanopore technology such as those manufactured by Oxford Nanopore Technologies (Oxford, UK) or Roche Sequencing Solutions (Santa Clara, Calif.) and any other presently existing or future DNA sequencing technology that does or does not involve sequencing by synthesis. The sequencing step may utilize platform-specific sequencing primers. Binding sites for these primers may be introduced in the method of the invention as described herein, i.e., by being a part of adaptors or amplification primers. In some embodiments, the sequencing platform does not require a specific extension primer.

In some embodiments, the invention is a method of determining the sequence of a double-stranded target nucleic acid by primer extension. In this embodiment, the sequencing primer is annealed to the sequencing primer binding site present in the circular molecule and a sequencing polymerase performs a sequencing read by extending the primer.

Notably, the method of the invention is applicable to a wide variety of target nucleic acid sizes.

In some embodiments, the sequencing step involves sequence analysis including a step of error correction. In some embodiments, sequence aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

In some embodiments, the invention is a kit for performing the method of the invention. The kit comprises one or more of the following: adaptors, universal amplification primers for generating adapted target nucleic acids, and a backbone oligonucleotide comprising sequences complementary to those in the adapted target nucleic acids. The kit may also comprise a DNA ligase (in some embodiments, T4 DNA ligase, Taq DNA ligase, or E. coli DNA ligase is used), a polynucleotide kinase and a DNA polymerase, such as an amplification polymerase or a sequencing polymerase. Non-limiting examples of polymerases include prokaryotic DNA polymerases (e.g. Pol I, Pol II, Pol III, Pol IV and Pol V), eukaryotic DNA polymerase, archaeal DNA polymerase, telomerase, reverse transcriptase and RNA polymerase. Reverse transcriptase is an RNA-dependent DNA polymerase which synthesizes DNA from an RNA template. The reverse transcriptase family contains both DNA polymerase functionality and RNase H functionality, which degrades RNA base-paired to DNA. In some embodiments, the kit also includes an exonuclease with a 5'-3'-activity such as a T5 exonuclease.

In some embodiments, the DNA polymerase possesses strand displacement activity and does not have a 5'-3'-exonudease activity. In some embodiments, Phi29 polymerase and its derivatives are used, see U.S. Pat. Nos. 5,001,050, 5,576,204, 7,858,747 and 8,921,086. In some embodiments, the polymerase has the 3'-5' exonudease activity that advantageously removes the 3'-A overhang from the amplicon strands.

EXAMPLES

Example 1

(Prophetic). Generating Single Stranded Circular Templates for Bacterial Whole Genome Sequencing In this example, DNA is extracted from a cultured bacterial isolate and first subjected to DNA damage repair, followed by mechanical or enzymatic fragmentation. The fragmented DNA may or may not be size selected. Following fragmentation, the DNA is end repaired and A-tailed, and the T-tailed adaptors with Gibson Assembly sequences (stitch) and sequencing primer binding sites are ligated onto each end. The adaptor ligated inserts are then mixed with a double-stranded DNA backbone flanked by Gibson Assembly adaptors complementary to the ones present in the insert molecules. During Gibson Assembly, an exonudease sequentially cleaves the 5' ends of the backbones and the inserts, revealing complementary Gibson Assembly adaptor ends. The backbone and the two ends of the insert molecule are allowed to anneal and then the gaps are filled with a DNA polymerase and covalently linked by ligation with a DNA ligase, generating a double-stranded circular molecule with sequencing primer binding sites on both strands. The double stranded DNA is then heat-denatured to create single stranded molecules ready for sequencing on a single molecule sequencing platform.

Example 2

(Prophetic). Generating Single Stranded Circular Templates for Single Molecule Sequencing from PCR Amplicons In this example, single stranded libraries for sequencing on single molecule sequencing platforms are generated starting from PCR amplicons. DNA damage repair and fragmentation are typically not required for PCR amplicons and the library prep process consists of end repair and A-tailing followed by ligation of T-tailed adaptors with Gibson Assembly sequences (stitch) and sequencing primer binding sites onto each end. The adaptor-ligated inserts are then mixed with a double-stranded DNA backbone flanked by Gibson Assembly adaptors complementary to the ones present in the insert molecules. During Gibson Assembly, an exonuclease sequentially removes the 5' ends of the backbones and the inserts, revealing complementary Gibson Assembly adaptor ends. The backbone and the two ends of the insert molecule are allowed to anneal and then the gaps are filled with a DNA polymerase and covalently linked by ligation with a DNA ligase, generating a double-stranded circular molecule with sequencing primer binding sites on both strands. The double stranded DNA is then denatured to create single stranded molecules ready for sequencing.

While the invention has been described in detail with reference to specific examples, it will be apparent to one skilled in the art that various modifications can be made within the scope of this invention. Thus the scope of the invention should not be limited by the examples described herein, but by the claims presented below.

The invention claimed is:

1. A method of forming a circular molecule from a target nucleic acid, the method comprising:
   (a) attaching adaptor sequences to the ends of the target nucleic acid to form an adapted target nucleic acid, wherein the adaptor comprises one or more nuclease-resistant modifications, wherein the one or more nuclease-resistant modifications is located one or more bases from the 5'-end;
   (b) contacting the adapted target nucleic acid with a double-stranded backbone nucleic acid comprising one or more nuclease-resistant modifications, wherein the one or more nuclease-resistant modifications is located one or more bases from each of the 5'-ends;
   (c) generating single-stranded overhangs in both the backbone and the adapted target nucleic acid by exonuclease digestion of the 5'-end ending at the modifications;
   (d) hybridizing the single-stranded overhangs of the backbone with the single-stranded overhangs of the adapted target nucleic acid; and
   (e) ligating the ends of the backbone with the ends of the adapted target nucleic acid to form a circular molecule.

2. The method of claim 1, wherein the adaptors are attached to the ends of the target nucleic acid by ligation.

3. The method of claim 1, wherein the adaptors are attached to the ends of the target nucleic acid by extension of a target specific bipartite primer comprising adaptor sequences in the 5'-portion.

4. The method of claim 3, wherein the adapted target nucleic acid is amplified prior to step (b).

5. The method of claim 1, further comprising a polymerase fill in step between steps (d) and (e).

6. The method of claim 1, wherein the adaptor or the backbone comprises at least one barcode.

7. The method of claim 1, wherein the backbone comprises a ligand for a capture moiety.

8. A method of sequencing a target nucleic acid, the method comprising the steps of:
   (a) forming circular nucleic acids according to claim 1, wherein the adaptor comprises a sequencing primer-binding site;

(b) separating the strands of the circular molecule to generate single-stranded circular molecules;
(c) annealing a sequencing primer to the sequencing primer-binding site in each of the single-stranded circular molecule; and
(d) extending the annealed sequencing primer thereby sequencing the target nucleic acid.

9. The method of claim 8, wherein the strands in step (b) are separated by heat or by chemical means.

10. The method of claim 8, wherein the strands in step (b) are separated by nicking one strand and removing the nicked strand by exonuclease digestion.

11. The method of claim 8, wherein sequencing utilizes a nanopore device.

\* \* \* \* \*